United States Patent [19]
Young

[11] Patent Number: 6,080,176
[45] Date of Patent: Jun. 27, 2000

[54] MEDICAL PUNCH WITH HIGH SHEAR ANGLE CUTTING EDGES

[75] Inventor: Larry Lee Young, Arab, Ala.

[73] Assignee: Atrion Medical Products, Inc., Arab, Ala.

[21] Appl. No.: 09/183,929

[22] Filed: Oct. 30, 1998

[51] Int. Cl.$^7$ .................................................. A61B 17/34
[52] U.S. Cl. ........................................... 606/185; 606/180
[58] Field of Search ..................................... 600/566, 567;
606/179, 185, 184, 180, 119, 174

[56] References Cited

U.S. PATENT DOCUMENTS

| | | |
|---|---|---|
| D. 372,310 | 7/1996 | Hartnett . |
| 4,018,228 | 4/1977 | Goosen . |
| 4,216,776 | 8/1980 | Downie et al. . |
| 4,895,166 | 1/1990 | Farr et al. ................................ 128/751 |
| 5,129,913 | 7/1992 | Ruppert . |
| 5,192,294 | 3/1993 | Blake . |
| 5,370,651 | 12/1994 | Summers ................................ 606/159 |
| 5,403,338 | 4/1995 | Milo . |
| 5,488,958 | 2/1996 | Topel et al. . |
| 5,556,408 | 9/1996 | Farhat ..................................... 606/180 |
| 5,569,276 | 10/1996 | Jang et al. .............................. 606/159 |
| 5,643,305 | 7/1997 | Al-Tameem . |
| 5,693,064 | 12/1997 | Arnold . |
| 5,788,651 | 8/1998 | Weilandt ................................. 600/567 |
| 5,827,316 | 10/1998 | Young et al. . |
| 5,879,358 | 3/1999 | Semm .................................... 606/119 |
| 5,947,978 | 9/1999 | Holsinger ............................... 606/110 |

*Primary Examiner*—Michael Buiz
*Assistant Examiner*—Anthony King
*Attorney, Agent, or Firm*—Trexler, Bushnell, Giangiorgi & Blackstone, Ltd.

[57] ABSTRACT

A medical punch having a plurality of cutting edges. The fact that the medical punch has a plurality of cutting edges provides, for example, that the medical punch can be used to achieve a clean and accurate cut, and provides that an excessive amount of hand pressure need not be employed to effect the cut.

34 Claims, 3 Drawing Sheets

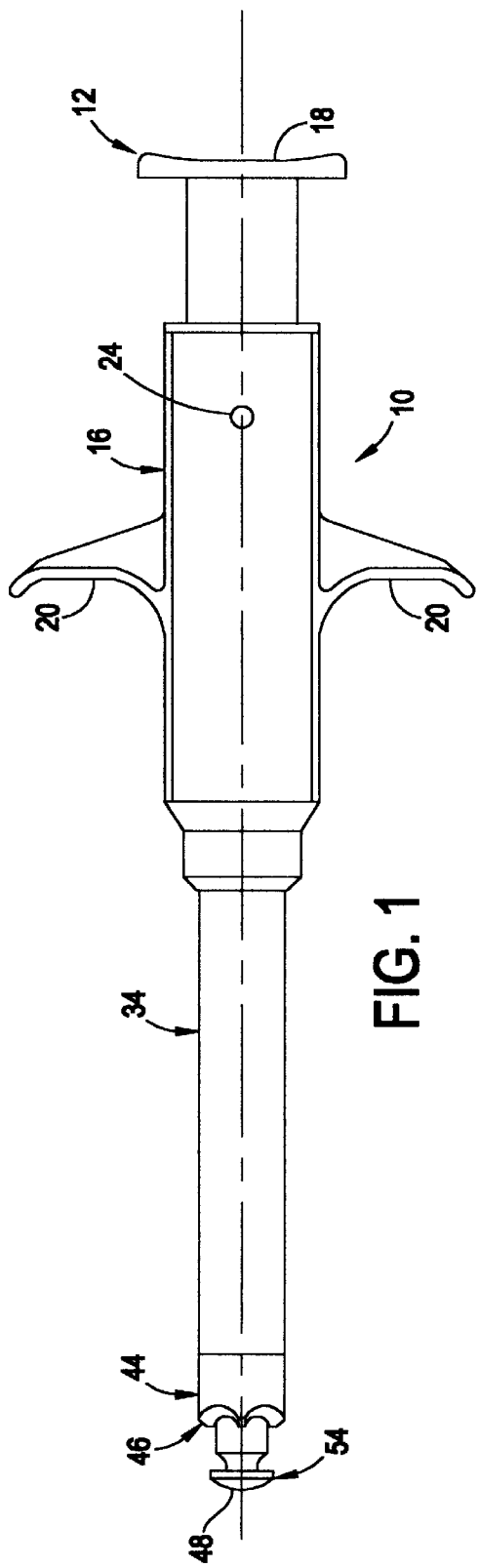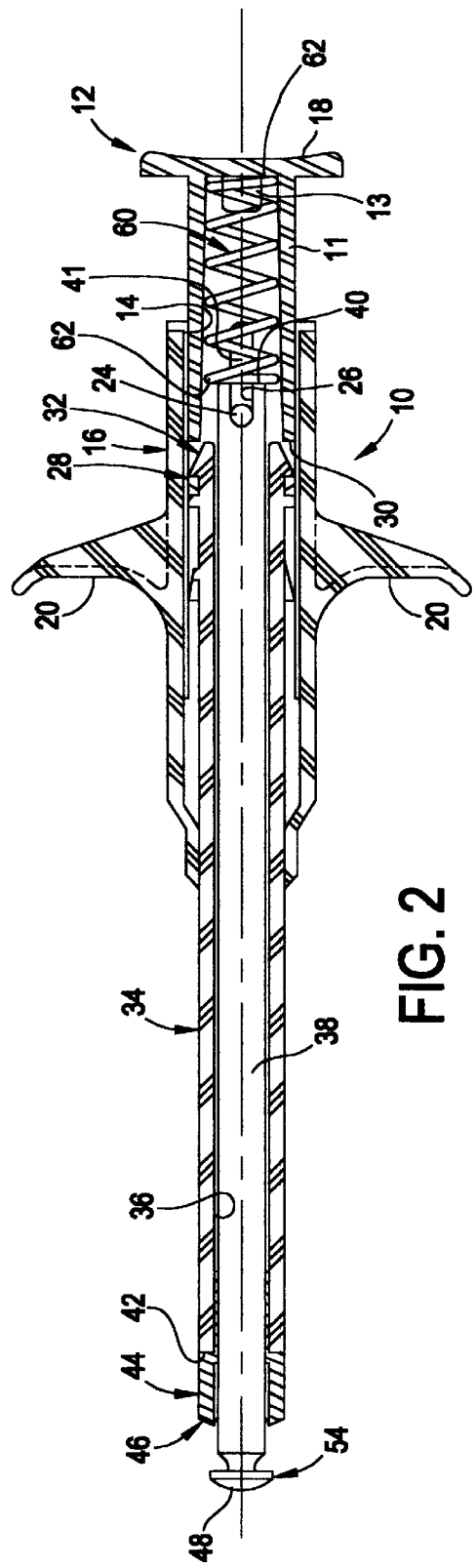

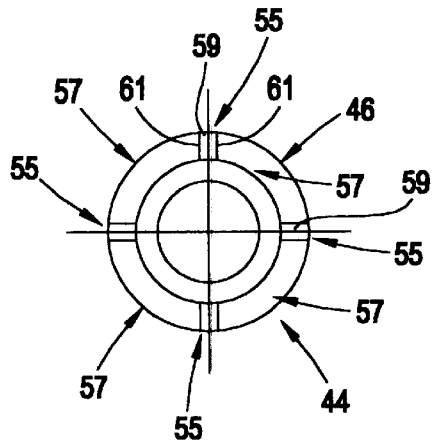
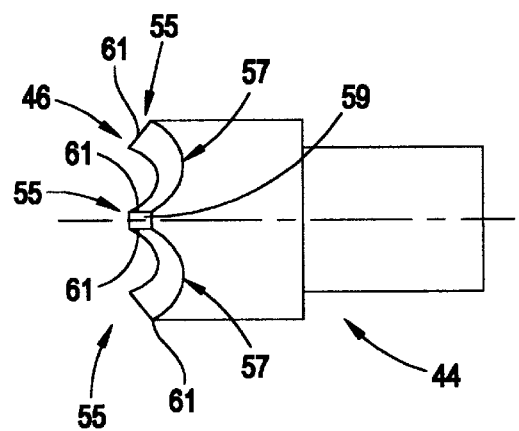
FIG. 3    FIG. 4
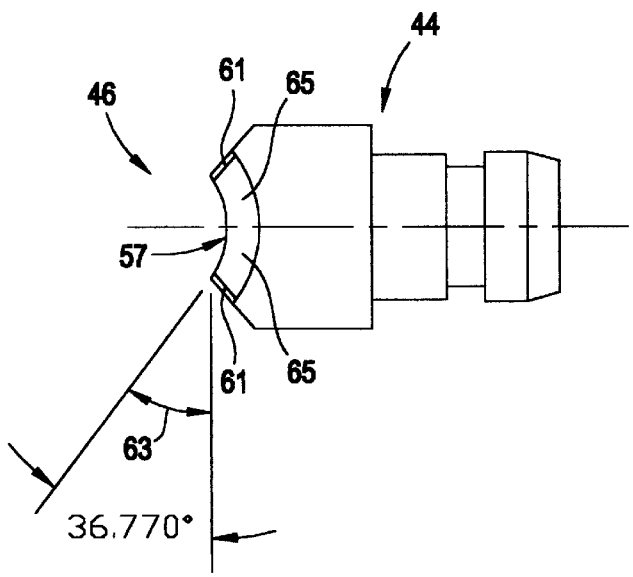
FIG. 5

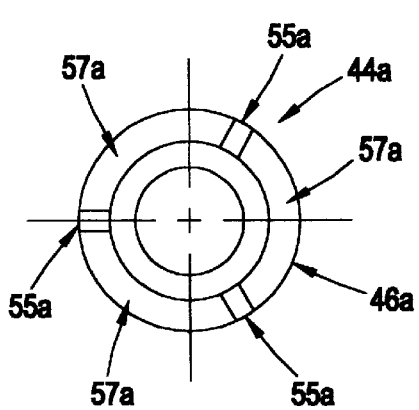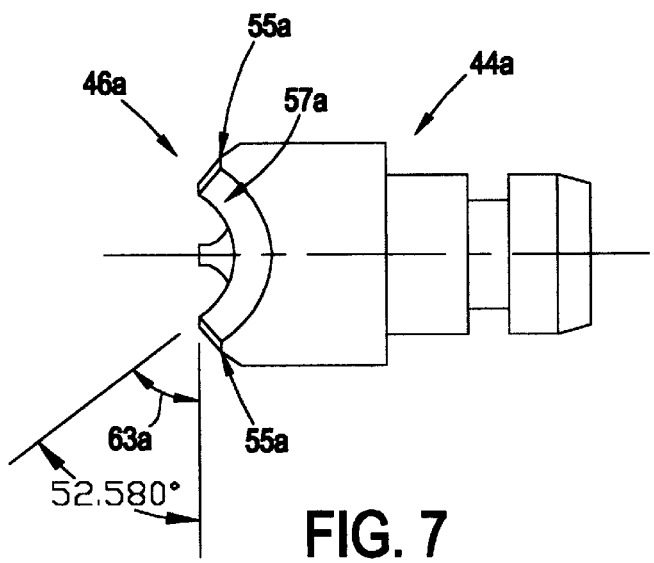
FIG. 6  FIG. 7
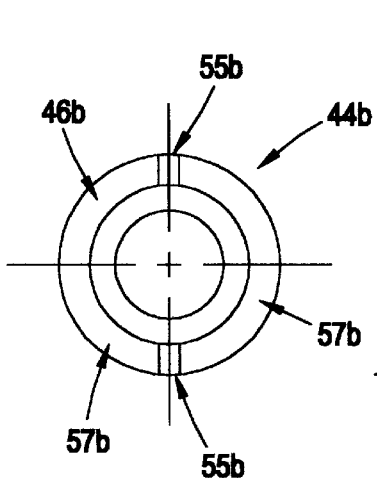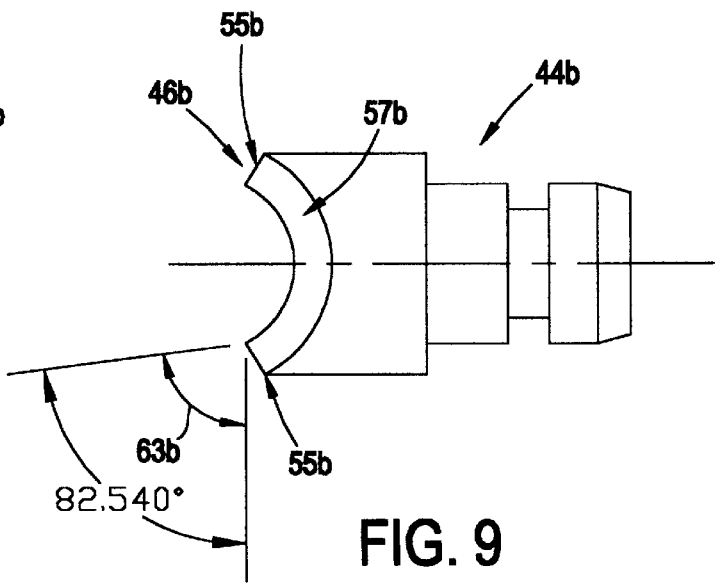
FIG. 8  FIG. 9

6,080,176

MEDICAL PUNCH WITH HIGH SHEAR ANGLE CUTTING EDGES

Medical punches are used in many situations to cut material, such as tissue. For example, there are situations where graft material is desired to be cut, and medical punches are employed to effect the cut. To effect a cut of material using a medical punch, surgical scalpels and/or scissors are first used to form an incision in the material. Typically, the medical punch will include an anvil, or other support, which is first inserted into the incision. Then, the surgeon takes his or her hand and approximates the thumb and opposed first and second fingers to push a thumb button while pulling a cross-bar. Consequently, a tube of the medical punch extends, and a cutting edge of the tube slides around the anvil, thus shearing the material. Finally, the anvil and cutting edge of the tube of the medical punch are withdrawn from the incision, and the cut has been effected. Examples of prior art medical punches can be found in the following U.S. Pat. Nos. 4,018,228; 4,216,776; 5,129,913; 5,192,294; 5,403,338 and U.S. Design Pat. No. D372,310.

The cutting edge of the tube in prior medical punches provides a flat cutting edge having effectively no shearing angle where the entire cutting edge cuts simultaneously into the material during the cutting operation. Because the medical punch accomplishes cutting of the material by shearing, and effects this shearing by sliding a flat cutting edge past the anvil, the material does not remain centralized and shifts slightly during the cut, and the resulting cut produced is not always extremely clean and accurate and some fraying may result. Moreover, because the material is often extremely durable and the cutting edge of the tube is flat thereby providing that the entire peripheral surface of the cut is effected at the same time, the surgeon must typically exert a lot of hand pressure to successfully manipulate the medical punch to effect the cut. Additionally, because the material does not remain centralized and shifts during the cutting operation, the material has a tendency to gather to one side or the other of the anvil of the device. This often causes the device to become jammed with the material jammed therein.

For the foregoing reasons, there is a need for an improved medical punch which does not have a tendency to jam, which can be used to obtain a very clean and accurate cut, without any fraying, and which can be used without having to exercise any excessive hand pressure. A much more effective medical punch is a medical punch designed and structured according to the present invention. The present invention is directed to substantially eliminate the difficulties encountered heretofore.

OBJECTS AND SUMMARY

Therefore, a general object satisfied by the present invention may be to provide a medical punch which does not tend to jam.

Another object satisfied by the present invention may be to provide a medical punch which can be used to obtain a clean and accurate cut of material with reduced fraying.

Still another object satisfied by the present invention may be to provide a medical punch which can be used without having to apply extensive hand pressure thereto.

Briefly, and in accordance with the foregoing, the present invention envisions a medical punch having a plurality of cutting edges. The device includes a hollow body member and a cutter on the end of the hollow body. The end of the cutter provides the cutting edges. A shaft is located in the hollow body member and has an anvil thereon for cooperation with the cutter. Sliding the hollow body member along the shaft causes the cutting edges to move past the anvil. The fact that the medical punch has a plurality of cutting edges provides that the device does not have a tendency to jam, and provides that the medical punch can be used to achieve a clean and accurate cut of material. The device also provides that and that extensive hand pressure need not be employed to effect the cut.

Preferably, the medical punch includes a thumb button which is pushable into a finger grip and is engaged with the hollow body member. The finger grip has a pin secured therein, and the pin is received within a slot on the thumb button. A compression spring is located within the thumb button having a first end engaged with the thumb button and a second end engaged with a shaft. The cutter is on the end of the hollow body member, and the hollow body member is slidable along the shaft. The shaft has an anvil at its end and is secured by the pin within the finger grip. Pushing the thumb button into the finger grip causes the hollow body to move generally axially relative to the shaft and causes the cutter to move past the anvil. Preferably, the cutter has at least three projections, and each of these projections provide a flat which contracts, supports and stabilizes the material initially during the cutting operation. The cutting edges are located between the projections and preferably provide a diminishing shear angle with an initial shear angle of about fifty-two degrees. The high initial shear angles and the fact that they diminish provides that it is easier to effect the desired cut using the medical punch.

BRIEF DESCRIPTION OF THE DRAWINGS

The organization and manner of the structure and function of the invention, together with further objects and advantages thereof, may be understood by reference to the following description taken in connection with the accompanying drawings, wherein like reference numerals identify like elements, and in which:

FIG. 1 is a side, elevational view of a medical punch which is in accordance with an embodiment of the present invention;

FIG. 2 is a cross-sectional view of the medical punch shown in FIG. 1;

FIG. 3 is a front, elevational view of a cutter component of the medical punch shown in FIGS. 1 and 2;

FIG. 4 is a side, elevational view of the cutter shown in FIG. 3;

FIG. 5 is a top, plan view of the cutter shown in FIG. 4;

FIG. 6 is a front, elevational view of a cutter which has three projections and which can be used in association with the medical punch shown in FIGS. 1 and 2;

FIG. 7 is a side, elevational view of the cutter shown in FIG. 6;

FIG. 8 is a front, elevational view of a cutter which has two projections and which can be used in association with the medical punch shown in FIGS. 1 and 2; and FIG. 9 is a side, elevational view of the cutter shown in FIG. 8.

DESCRIPTION OF EMBODIMENTS OF THE INVENTION

While the present invention may be susceptible to embodiment in different forms, there is shown in the drawings, and herein will be described in detail, embodiments with the understanding that the present description is to be considered an exemplification of the principles of the invention and is not intended to limit the invention to that as illustrated and described herein.

Shown in FIGS. 1 and 2 is a medical punch 10 which is in accordance with an embodiment of the present invention. Instead of having a single cutting edge with effectively no shear angle, the medical punch 10 includes a plurality of cutting edges each having a diminishing shear angle. As a result, the medical punch 10 can be used to achieve a clean and accurate cut of material. Additionally, the medical punch 10 provides that an excessive amount of hand pressure need not be employed to effect the cut. Furthermore, the medical punch 10 does not tend to jam because the material is generally kept centralized with respect to the device during the cutting operation.

The medical punch 10 is shaped and designed to be utilized by a surgeon using one of his or her hands. The medical punch 10 includes a thumb button 12 pushable into a central opening 14 in a finger grip body 16. The thumb button 12 includes a thumb seat 18 which is shaped to be engaged by the thumb of the surgeon, and the thumb button 12 includes a hollow cylindrical portion 11 which extends into the central opening 14 of the finger grip body 16. The finger grip body 16 includes finger seats 20 which are shaped to be engaged by the first and second fingers of the surgeon. Secured in the central opening 14 of the finger grip body 16 is a pin 24. The pin 24 is received in slots 26 formed in the hollow cylindrical portion 11 of the thumb button 12. The slots 26 slide across the pin 24 when the thumb button 12 is pushed into the opening 14 of the finger grip 16. As the thumb button 12 is pushed into the opening 14 in the finger grip 16, the pin 24 restricts the extent to which the thumb button 12 can be pushed into the central opening 14.

A bottom portion 28 of the thumb button 12 has an opening 30 for snap-on, securable engagement with a top portion 32 of a hollow body member 34. This snap-on engagement provides that the hollow body member 34 moves along with the thumb button 12 when the thumb button 12 is pushed into, or pulled out from, the central opening 14 of the finger grip body 16.

The hollow body member 34 has a central throughbore 36 through which extends a shaft 38. The pin 24 extends through, and secures, a top portion 40 of the shaft 38. This securement of the pin 24 with the top portion 40 of the shaft 38 provides that the shaft 38 remains stationary with respect to the finger grip body 16 when the thumb button 12 is pushed into the central opening 14 in the finger grip body 16.

Within the thumb button 12 sits a compression spring 60. A top 62 of the compression spring 60 is engaged with a flange 13 within the hollow cylindrical portion 11 of the thumb button 12, and a bottom 64 of the compression spring 60 is engaged with a shoulder 41 on the top portion 40 of the shaft 38. The compression spring 60 works to urge the thumb button 12 out from the central opening 14 of the finger grip body 16 whenever the thumb button 12 is pushed therein. Providing the compressing spring 60 within the thumb button 12 permits the finger grip body 16 to be designed and shaped such that the finger seats 20 are relatively close together. As a result, the medical punch 10 is easier to use because it more easily fits in the surgeon's hand.

When the thumb button 12 is pushed into the finger grip body 16, the shaft 38 does not move because the top portion 40 of the shaft is secured by the pin 24. However, the securable engagement of the bottom portion 28 of the thumb button 12 with the top portion 32 of the hollow body member 34 provides that the hollow body member 34 slides along the shaft 38 as the thumb button 12 is pushed. Therefore, the hollow body member 34 slides along the shaft 38, which remains stationary, whenever the thumb button 12 is pushed into the finger grip body 16.

At the end 42 of the hollow body member 34 is a cutter 44 which preferably comprises a barrel pin having an end portion 46. Also, the end 48 of the shaft 38 provides an anvil 54 which preferably has an edge which provides a crisp 90° angle. When the thumb button 12 is pushed into the central opening 14 of the finger grip body 16, the cutter 44 slides along with the hollow body member 34 in relation to the shaft 38, and the end portion 46 of the cutter 44 moves toward and across the anvil 54 thereby effecting the desired cut.

The end portion 46 of the cutter 44 provides a plurality of projections or protrusions and a plurality of cutting edges each located between adjacent projections. In other words, the end portion 46 provides a plurality of alternating peaks and valleys which in effect provide a plurality of projections and cutting edges for engaging the material to be cut. The projections support, stabilize, centralize and eventually pierce the material during the cut, and the cutting edges provide diminishing shear angles while having a relatively high initial shear angle. The high initial shear angle provides for a clean piercing of the tissue by the projections initially during the cutting operation and the diminishing shear angles provide that the cutting action is essentially scissor-like.

FIGS. 1–5 illustrate the situation where the end portion 46 of the cutter 44 is provided with four projections 55 and four cutting edges 57. While each projection 55 may be provided as being essentially a single pointed edge, it is preferred that each projection 55 be a chisel projection in that it includes a flat portion 59 which extends between two edges 61 (see FIGS. 3 and 4). The flats provide for increased stability of the material during the cut. Each of the edges 61 intersect an adjacent cutting edge 57 to provide an initial shear angle 63. The initial shear angle is the angle at which the cutting edge 57 intersects an adjacent projection 55. Therefore, if the projections 55 are provided as having two edges 61, the initial shear angle is the angle at which a cutting edge 57 intersects an edge 61 of a projection 55. On the other hand, if each projection is provided as being a single pointed edge, the initial shear angle would be the angle at which the cutting edge intersects this edge.

Each cutting edge 57 is preferably elliptical in shape as it extends from one projection to another adjacent projection. This shape effectively provides that each cutting edge 57 has a diminishing shear angle. Specifically, each cutting edge 57 essentially provides two initial shear angles—one initial shear angle for each shearing front 65 of the cutting edge 57 (see FIG. 5)—and each shearing front 65 provides a diminishing shear angle which effectively becomes zero as one shearing front meets the other along a single cutting edge 57. Each cutting edge 57 provides two shearing fronts 65 which meet generally in the middle of the cutting edge 57. Preferably each cutting edge 57 provides two initial shear angles 63—one at each shearing front 65—and each initial shear angle 63 is equal to the other. Specifically, FIGS. 1–5 depict the situation where each cutting edge is provided as having two initial shear angles 63 which are generally equal to each other and are each approximately 36.770° (see FIG. 5 which identifies one of the shear angles 63).

As shown in FIGS. 1, 3 and 4, each cutting edge 57 and each projection 55 of the cutter 44 may be beveled. For example, each may have a 52° bevel angle. The bevels provide for more effective piercing (with regard to the projections 55) and cutting (with regard to cutting edges 57) surfaces. The bevels as well as the cutting edges 57 themselves may be formed on the cutter 44 using a grinding wheel.

As will be described more fully later herein, each projection 55 supports, grips stabilizes and centralizes the tissue or material to be cut by the medical punch 10, and the projections 55 initiate a cutting action by piercing prior to shearing by the cutting edges 57. As mentioned, it is preferred that each projection be provided with a flat portion. The flat portions work to hold the tissue steady and generally centralized when the end 46 of the cutter 44 first begins to move past the anvil 54. This functions to hold the tissue steady during the cutting operation and keeps the tissue or material centralized during the cutting operation. As opposed to stabilizing the material and keeping it generally centralized, shiftings of the tissue during the cut may cause the material to collect on one side or the other of the cutter 44 causing the device to jam with the portion of the material which has been cut being retained in the device.

As the thumb button 12 is further pushed, each cutting edge 57 shears the tissue along each of its two shearing fronts 65 until the cut meets at the intersection of the shearing fronts 65 which is generally at the middle of the cutting edge 57 (i.e. at the bottom of the valley), and at which point the shear angle is preferably generally zero. At this time, further pushing of the thumb button 12 completes the cutting operation. The multiple cutting edges 57 provide that the tissue or material is cut with a shearing action as the cutter 44 advances against the anvil 54, but not all at once as is done by a cutter which provides a flat cutting edge with effectively no shearing angle. Instead, only a portion of the peripheral edge of the cut is made at one time, and this provides that it takes less hand pressure to actuate the medical punch 10 during the cutting operation. For example, providing four cutting edges 57 with initial shearing angles 63 of 36.770° and with a 52° bevel angle, as shown in FIGS. 1–5, yields about a 50% reduction in the hand force it takes to effect the cut—reducing a 40 to 50 pound required actuating force to 20 pounds or less in order to effect a cut using a medical punch which produces a 5 mm cut. Additionally, a cleaner cut is achieved.

While FIGS. 1–5 depict the situation where the end 46 of the cutter 44 is provided with four projections 55, it is possible to provide that the end 46 has either more or less projections. For example, FIGS. 6 and 7 illustrate a cutter 44a which can be used in connection with the medical punch 10 shown in FIGS. 1 and 2 where the cutter 44a has an end portion 46a which includes three projections 55a and three cutting edges 57a. In such a case, as indicated in FIG. 7, each shearing angle 63a can be provided as being approximately 52.580°.

FIGS. 8 and 9 illustrate yet another cutter 44b which can be used in connection with the medical punch 10 shown in FIGS. 1 and 2. The cutter 44b has an end portion 46b which includes two projections 55b and two cutting edges 57b. In such a case, as indicated in FIG. 9, each shearing angle 63b can be provided as being approximately 82.540°. While it is possible to provide that the end portion of the cutter has two projections as shown in FIGS. 8 and 9, it is preferred that the end portion of the cutter include at least three projections, as this configuration renders more stability during the cutting operation and tends to more effectively keep the material centralized during the cutting operation. Specifically, providing three or more projections provides that the end portion of the cutter can better hold and keep the tissue centralized during the cutting operation thereby providing a cleaner cut and rending that the device is less susceptible to jamming. Regardless of how many projections are provided, it is preferred that the initial shear angles of the cutting edges be provided as being between 0° and 90° and that each cutting edge provide effectively two diminishing shear angles which meet to provide a shear angle of effectively zero.

Preferably, the thumb button 12, finger grip body 16, and hollow body member 34 of the medical punch 10 are all comprised of plastic, and the pin 24, shaft 38, compression spring 60, and the cutter 44 of the medical punch 10 are all comprised of metal. However, these compositions are, of course, not imperative to the present invention.

While some reference was made to the general operation of the medical punch 10 in order to adequately describe its structure, the operation and functioning of the medical punch 10 will now be more fully described. To operate the medical punch 10, a surgeon (not shown) would grab the medical punch 10 in his or her hand, would place a thumb on the seat 18 of the thumb button 12, and would place both an index finger tip and a middle finger tip seats 20 of the finger grip body 16. After a small incision has been made in the material, the surgeon would maneuver the medical punch 10 so that the anvil 54 on the end 48 of the shaft 38 is inserted into the incision.

After the anvil 54 is inserted into the small incision in the material, the surgeon would push on the thumb seat 18 with his or her thumb while holding the finger seats 20 with his or her fingers. This pushing of the thumb button 12 drives the thumb button 12 into the central opening 14 in the finger grip body 16. As the thumb button 12 is pushed into the finger grip body 16, the slots 26 on the thumb button 12 ride along the pin 24 in the finger grip 16. Additionally, the hollow body member 34 slides along the shaft 38 because the top portion 32 of the hollow body member 34 is in securable, snap-on engagement with the opening 30 in the bottom portion 28 of the thumb button 12. As the thumb button 12 is pushed into the finger grip 16, the compression spring 60 compresses within the thumb button 12 against the shaft 38, and the shaft 38 remains stationary because of securement by the pin 24 within the finger grip 16. Since the hollow body member 34 slides along the shaft 38, the cutter 44 at the end 42 of the shaft 38 moves toward the anvil 54 at the end 48 of the shaft 38.

As the thumb button 12 is pushed, the hollow body member 34 slides along the shaft 38, and the cutter 44 on the hollow body member 34 slides toward the anvil 54. Initially, the projections 55 (or 55a or 55b) engage the material and then pierce into the material as the thumb button 12 is more fully pushed. This provides that the material is stabilized and generally kept centralized during the cutting operation. Then, the cutting edges 57 (or 57a or 57b) begin shearing, in a scissor-like action, the tissue at two points-at each shearing front—until the thumb button 12 is pressed sufficiently to provide that the cutting proceeds to the intersection of the shearing fronts, generally in the middle of the cutting edges 57 (or 57a or 57b) where the shearing angles have diminished to effectively zero. At this time, the cutter 44 slides past the anvil 54, thus severing the material. Subsequently, the medical punch 10 can be withdrawn from the incision such that the anvil 54, the cutter 44 and the severed portion are collectively withdrawn. Then, the thumb button 12 can be released, and the compression spring 60 urges the thumb button 12 from the finger grip body 16. Thus, the cutter 44 retracts from the anvil 54 causing the severed portion of the material to drop away from the medical punch 10.

Should the severed portion of the material get caught between the anvil and the cutter 44, thus temporarily jamming the medical punch 10, the medical punch 10 provides that the surgeon can pull on the thumb button 12 to release the severed portion. Because the thumb button 12 is in snap-on, securing engagement with the hollow body member 34, pulling the thumb button 12 causes the hollow body member 34 to slide in relation to the shaft 38. The cutter 44 slides away from the anvil 54 when the thumb button 12 is pulled. Consequently, pulling the thumb button 12 from the finger grip 16 should cause the severed portion to dislodge from between the anvil 54 and the cutter 44, and drop away from the medical punch 10.

The medical punch 10 provides that each projection supports, grips and generally keeps centralized the tissue or material to be cut by the medical punch 10, and that the projections initiate a cutting action by piercing prior to the shearing by the cutting edges. The multiple cutting edges and shearing fronts provide that the tissue or material is cut with a shearing action as the cutter 44 advances against the anvil 54. However, the entire peripheral edge of the cut (i.e. the entire edge of the hole being formed) is not effected at once. Instead, the cut is effected gradually as the thumb button 12 is pressed. For example, in the situation shown in FIGS. 1–5 where four projections 55 are provided on the cutter 44, the shearing action is effected at eight different areas (at each shearing front 65). As the thumb button 12 is pressed, the cuts being made by the eight shearing fronts 65 intersect, thereby effecting the cutting operation in a gradual manner. By cutting only a portion of the peripheral edge of the cut at one time, it takes less hand pressure on the medical punch 10 to effect the cutting operation. Additionally, by cutting only a portion of the peripheral edge of the cut at one time, the medical punch 10 produces a cleaner cut with a more precise hole in the material being achieved. Furthermore, by providing that the tissue is stabilized by the projections 55 (or 55a or 55b) and kept generally centralized during the cutting operation, the tissue does not tend to shift, thereby producing a better cut and providing that the device is less susceptible to jamming.

While several embodiments of the present invention are shown and described herein, it is envisioned that those skilled in the art may devise various modifications and equivalents without departing from the spirit and scope of the invention as defined by the appended claims.

The invention claimed is:

1. A medical punch comprising: a hollow body member having an end; a cutter on said end of said hollow body, said cutter including a plurality of projections and a plurality of cutting edges, wherein each cutting edge is located between two projections and each projection is located between two cutting edges, each of said projections including a flat portion between two edges which intersect cutting edges; and a shaft located in said hollow body member and having an anvil thereon for cooperation with said cutter, wherein sliding said hollow body member along said shaft causes said cutting edges to move past said anvil.

2. The medical punch as defined in claim 1, further comprising a finger grip and a thumb button pushable into said finger grip, wherein said thumb button is coupled to said hollow body member, and wherein said thumb button pushes said hollow body member causing said hollow body member to slide along said shaft when said thumb button is pushed into said finger grip.

3. The medical punch as defined in claim 2, further comprising a pin secured within said finger grip, wherein said pin secures said shaft, and wherein said pin is received in a slot on said thumb button.

4. The medical punch as defined in claim 3, further comprising a compression spring within said thumb button, said spring having a first end engaged with said thumb button and having a second end engaged with said shaft.

5. The medical punch as defined in claim 3, wherein said thumb button and said hollow body member are coupled such that said thumb button pulls on said hollow body member causing said hollow body member to slide along said shaft when said thumb button is pulled from said finger grip.

6. The medical punch as defined in claim 4, wherein said thumb button and said hollow body member are coupled such that said thumb button pulls on said hollow body member causing said hollow body member to slide along said shaft when said thumb button is pulled from said finger grip.

7. The medical punch as defined in claim 2, further comprising a compression spring within said thumb button, said spring having a first end engaged with said thumb button and having a second end engaged with said shaft.

8. The medical punch as defined in claim 2, wherein said thumb button and said hollow body member are coupled such that said thumb button pulls on said hollow body member causing said hollow body member to slide along said shaft when said thumb button is pulled from said finger grip.

9. The medical punch as defined in claim 1, wherein said cutter includes at least three projections.

10. The medical punch as defined in claim 1, wherein each cutting edge has an initial shear angle of between 30 and 40 degrees and diminishes thereafter.

11. The medical punch as defined in claim 1, wherein each cutting edge has an initial shear angle of between 45 and 55 degrees and diminishes thereafter.

12. The medical punch as defined in claim 1, wherein each cutting edge has an initial shear angle of between 80 and 90 degrees and diminishes thereafter.

13. The medical punch as defined in claim 1, wherein each cutting edge is beveled.

14. The medical punch as defined in claim 1, wherein each projection is beveled.

15. The medical punch as defined in claim 1, wherein each cutting edge and projection is beveled.

16. A medical punch comprising: a hollow body member having an end; a cutter on said end of said hollow body, said cutter including a cutting edge having a plurality of alternating peaks and valleys; and a shaft located in said hollow body member and having an anvil thereon for cooperation with said cutting edge, wherein sliding said hollow body member along said shaft causes said cutting edge to move past said anvil, and wherein each of said peaks includes a substantially flat portion located between two edges.

17. The medical punch as defined in claim 16, wherein said cutting edge of said cutter includes at least three peaks.

18. The medical punch as defined in claim 16, wherein each cutting edge is beveled.

19. The medical punch as defined in claim 16, wherein each projection is beveled.

20. The medical punch as defined in claim 16, wherein each cutting edge and projection is beveled.

21. A medical punch comprising: a finger grip; a pin secured within said finger grip; a hollow body having a first end and a second end; a thumb button having a slot thereon, said thumb button in contact with said first end of said hollow body, said thumb button pushable into said finger grip, said pin secured within said finger grip received within said slot on said thumb button; a shaft within said hollow body, said shaft having an end; a compression spring within said finger grip in contact with said shaft; a cutter on said second end of said hollow body, said cutter having a plurality of cutting edges and a plurality of projections, wherein each cutting edge is located between two projections and each projection is located between two cutting edges, each of said projections including a flat portion between two edges which intersect cutting edges, said pin securing said shaft, said hollow body slidable along said shaft; and an anvil on said end of said shaft, wherein pressing said thumb button into said finger grip causes said hollow body to move along said shaft and causes said cutting edges to slide across said anvil.

22. The medical punch as defined in claim 21, wherein each cutting edge is beveled.

23. The medical punch as defined in claim 21, wherein each projection is beveled.

24. The medical punch as defined in claim 21, wherein each cutting edge and projection is beveled.

25. A medical punch comprising: a hollow body member having an end; a cutter on said end of said hollow body, said cutter including a plurality of material-supporting projections and a plurality of cutting edges, wherein each cutting edge is located between two projections and each projection is located between two cutting edges, each of said projections including a flat portion between two edges which intersect cutting edges; and a shaft located in said hollow body member and having an anvil thereon for cooperation with said cutter, wherein sliding said hollow body member along said shaft causes said cutting edges to move past said anvil.

26. The medical punch as defined in claim 25, wherein each cutting edge is beveled.

27. The medical punch as defined in claim 25, wherein each projection is beveled.

28. The medical punch as defined in claim 25, wherein each cutting edge and projection is beveled.

29. A medical punch comprising: a hollow body member having an end; a cutter on said end of said hollow body, said cutter including a plurality of material-piercing projections and a plurality of cutting edges, wherein each cutting edge is located between two projections and each projection is located between two cutting edges, each of said projections including a flat portion between two edges which intersect cutting edges; and a shaft located in said hollow body member and having an anvil thereon for cooperation with said cutter, wherein sliding said hollow body member along said shaft causes said cutting edges to move past said anvil.

30. The medical punch as defined in claim 29, wherein each cutting edge is beveled.

31. The medical punch as defined in claim 29, wherein each projection is beveled.

32. The medical punch as defined in claim 29, wherein each cutting edge and projection is beveled.

33. A medical punch comprising: a hollow body member having an end; a cutter on said end of said hollow body, said cutter including a plurality of cutting edges, wherein each cutting edge is beveled; and a shaft located in said hollow body member and having an anvil thereon for cooperation with said cutter, wherein sliding said hollow body member along said shaft causes said cutting edges to move past said anvil.

34. The medical punch as defined in claim 33, said cutter including a plurality of projections, wherein each projection is beveled.

\* \* \* \* \*

UNITED STATES PATENT AND TRADEMARK OFFICE
CERTIFICATE OF CORRECTION

PATENT NO. : 6,080,176
DATED : June 27, 2000
INVENTOR(S) : Larry Lee Young

It is certified that error appears in the above-identified patent and that said Letters Patent is hereby corrected as shown below:

Column 1, Line 3 -- BACKGROUND

The present invention relates generally to medical punches such as aortic punches for use during heart surgery, and more specifically relates to a novel medical punch having a plurality of cutting edges. --

Signed and Sealed this

Third Day of April, 2001

Attest:

NICHOLAS P. GODICI

Attesting Officer

Acting Director of the United States Patent and Trademark Office